(12) United States Patent
Hoffmann et al.

(10) Patent No.: US 8,075,912 B2
(45) Date of Patent: Dec. 13, 2011

(54) AUTODESTRUCTIVE TRANSDERMAL THERAPEUTIC SYSTEM

(75) Inventors: Hans-Rainer Hoffmann, Neuwied (DE); Thomas Hille, Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 472 days.

(21) Appl. No.: 12/301,244

(22) PCT Filed: May 22, 2007

(86) PCT No.: PCT/EP2007/004516
§ 371 (c)(1),
(2), (4) Date: Nov. 18, 2008

(87) PCT Pub. No.: WO2007/137732
PCT Pub. Date: Dec. 6, 2007

(65) Prior Publication Data
US 2011/0159076 A1 Jun. 30, 2011

(30) Foreign Application Priority Data

May 31, 2006 (DE) .......................... 10 2006 025 282

(51) Int. Cl.
*A61K 9/70* (2006.01)
*A61K 9/00* (2006.01)
*A61K 9/14* (2006.01)
*A61K 33/32* (2006.01)
*A61K 31/44* (2006.01)

(52) U.S. Cl. ......... 424/449; 424/484; 424/640; 514/282
(58) Field of Classification Search .................. 424/449, 424/400, 484, 640; 514/282
See application file for complete search history.

(56) References Cited

U.S. PATENT DOCUMENTS

| 4,917,676 | A | 4/1990 | Heiber et al. |
| 5,149,538 | A | 9/1992 | Granger et al. |
| 2004/0241218 | A1 | 12/2004 | Tavares et al. |
| 2005/0163717 | A1 | 7/2005 | Anderson et al. |
| 2007/0014839 | A1 * | 1/2007 | Bracht .......................... 424/449 |

FOREIGN PATENT DOCUMENTS

| WO | WO 90/04965 A1 | 5/1990 |
| WO | WO 02/085268 A1 | 10/2002 |
| WO | WO 02/087482 A1 | 11/2002 |
| WO | WO 02/094172 A2 | 11/2002 |
| WO | WO 2004/037259 A1 | 5/2004 |
| WO | WO 2004/098568 A2 | 11/2004 |
| WO | WO 2004/098576 A1 | 11/2004 |
| WO | WO 2005/041883 A2 | 5/2005 |
| WO | WO 2005/070003 A2 | 8/2005 |
| WO | WO 2005/102294 A2 | 11/2005 |

OTHER PUBLICATIONS

S. Kandavilli et al., "Polymers in Transdermal Drug Delivery Systems", Pharmaceutical Technology, May 2002, pp. 62-80.

* cited by examiner

*Primary Examiner* — Johann Richter
*Assistant Examiner* — Abigail Fisher
(74) *Attorney, Agent, or Firm* — ProPat, L.L.C.

(57) ABSTRACT

The invention relates to a transdermal therapeutic system (TTS), preferably in the form of a transdermal plaster, that contains an active substance and an agent which can destroy the active substance. The TTS further includes a means of bringing the active substance, e.g. buprenorphine, and the agent, e.g. potassium permanganate, into contact when the TTS is removed from the skin of the patient, thereby causing the active substance to be destroyed.

14 Claims, No Drawings

AUTODESTRUCTIVE TRANSDERMAL THERAPEUTIC SYSTEM

CROSS-REFERENCE TO RELATED APPLICATIONS

This application is being filed under Rule 1.371 as a National Stage Application of pending International Application No. PCT/EP2007/004516 filed May 22, 2007, which claims priority to the following parent application: German Patent Application No. 10 2006 025 282.9, filed May 31, 2006. Both International Application No. PCT/EP2007/004516 and German Patent Application No. 10 2006 025 282.9 are hereby incorporated by reference herein in their entirety.

FIELD OF THE INVENTION

The invention relates to a transdermal therapeutic system, or else called transdermal patch (TTS), which is self-destroying after use. The TTS of the invention comprises a therapeutic active ingredient, preferably from the group of analgesics.

BACKGROUND OF THE INVENTION

Thus, for example, TTS with the active ingredients buprenorphine and fentanyl are the pharmaceutical forms of choice for the treatment of chronic pain in long-term therapy. The continuous delivery of these highly effective analgesics through the skin provides a continuous supply of analgesic to a patient with pain, so that plasma peaks and plasma troughs are avoided.

This has the advantage that both side effects due to overdoses, but also states of pain due to undersupply, are avoided by a low but sufficient plasma concentration of the active ingredient. The skilled worker knows for example of the commercial products TRANSTEC®, but also DUROGESIC® or DUROGESIC® SMAT, which have proved useful in pain therapy for some time. The disadvantage of TTS in pain therapy is that to maintain the so-called concentration gradient and thus the desired plasma level of the active ingredient during the period when the TTS is applied, it is always necessary for more active ingredient to be present in the TTS than is actually delivered to the patient. This results in worn TTS representing a potential for abuse by, for example, members of the drug scene, because these groups of people are perfectly capable of collecting used TTS and extracting them with the most primitive means in order to obtain the active ingredient still present therein and misuse it for appeasing the drug addiction.

There has in the past therefore been no lack of attempts to suppress this misuse by advising patients to cut up the worn patch and put it down the toilet to reach the sewerage system. The disadvantage of this method is that neither the legislature nor the pharmaceutical manufacturer can guarantee that this procedure is in fact followed by patients. For this reason, TTS which contained an antagonist, besides the active ingredient, have been developed (e.g. WO 2004/098576, WO 90/04965, WO 2004/037259). The intention thereby was to prevent or at least markedly impede the obtaining or extraction, described above, of the analgesic active ingredient from used TTS. These protective measures have, however, not proved adequate for preventing medicament abuse because it is still possible with relatively simple means to separate the actual active ingredient from the antagonist by fractional precipitation.

WO 02/094172 describes a system for preventing misuse of dosage systems, but the active ingredient in this system still remains activatable and is not destroyed. Likewise in WO 2005/070003; the active ingredient therein is merely absorbed, which still makes the possibility of separation from the ab/adsorbent possible. Finally, WO 2004/098568 describes an "abuse-resistant" transdermal dosage system. Just like the other known systems of this type, once again the active ingredient is not destroyed but is merely neutralized in effect by an antagonist.

SUMMARY OF ADVANTAGEOUS EMBODIMENTS OF THE INVENTION

The present invention was therefore based on the object of providing a TTS with which the described medicament abuse can be at least substantially precluded after use.

This object is achieved by providing a TTS, preferably in the form of a transdermal patch to be applied to the surface of the patient's skin, that destroys itself—automatically—after use, i.e. after removal of the TTS from the surface of the patient's skin. Self-destroying TTS means primarily that the contained active pharmaceutical ingredient is destroyed, chemically reacted and/or made useless after use. It is moreover ensured that this destruction process is not started before or during application of the TTS.

DETAILED DESCRIPTION OF ADVANTAGEOUS EMBODIMENTS OF THE INVENTION

The invention thus relates to a transdermal therapeutic system (TTS), preferably in the form of a transdermal patch, which comprises at least one therapeutic active ingredient and a substance or a substance mixture (agent) which can destroy the active ingredient, or make it useless, preferably by chemical reaction, where active ingredient and agent are separated from one another (preferably spatially separated) and where the TTS comprises at least one means by which active ingredient and agent come into contact with one another when the TTS is removed from the patient's skin, and the active ingredient is destroyed by this contact or is made useless in terms of its activity.

The agent may be a substance or a substance mixture which may in turn be in the form of a solid, solution, gel, dispersion or other states. The agent is preferably a substance which chemically reacts with the active ingredient and destroys it thereby, especially a chemical oxidizing agent such as, for example, inorganic reagents such as permanganates, e.g. potassium permanganate, manganese dioxide, lead dioxide, lead tetraacetate, cerium(IV) salts, chromates, chromic acid, osmium tetroxide, nitric acid, nitrites such as potassium nitrite, selenium dioxide, hydrogen peroxide and other peroxo compounds, bromine, chlorine, hypohalides or sulfur; preferably potassium permanganate, hydrogen peroxide and potassium nitrite; organic oxidants such as dimethyl sulfoxide, N-bromosuccininide, quinones, hypervalent iodine compounds, peracids and peresters, but also enzymes. The agent for a given active ingredient is preferably selected on the basis of its chemical reactivity with the active ingredient.

The active ingredient is preferably an active ingredient from the group of analgesics such as, for example, narcotics. Mention should preferably be made of morphine derivatives, heroin and buprenorphine, or fentanyl and its derivatives sufentanyl and alfentanyl. It is also possible in principle to use all other active ingredient/agent combinations for which application via a TTS is the suitable dosage form. The means by which active ingredient and agent come into contact with one another and/or react chemically with one another after removal of the patch/TTS from the patient's skin can likewise appear in diverse forms. It must be ensured that the means complies with its function on every removal of the TTS, irrespective of the direction of pulling off. The means is moreover adapted to the form in which the agent is present (e.g. as solution in a bag). The means is preferably fixed inside on the outer top layer of the TTS, e.g. by bonding to the inside of the top layer. Examples of means of the invention depending on the state of the agent will be evident to the skilled worker from the selection of the agent and its form of accommodation in the TTS.

Otherwise, the materials known to the skilled worker for such systems can be used to produce the TTS or transdermal patch of the invention.

The TTS of the invention preferably has a layer structure, for example as illustrated in the exemplary embodiment. The TTS may be in the form of a matrix patch in which the active ingredient is present in a matrix which consists of one or more layers and which lies directly on the skin with the aid of an adhesive layer. In the likewise possible embodiment of membrane patch, an adhesive membrane is located between the active ingredient reservoir and the skin and controls the delivery of active ingredient into the uppermost layer of the skin, the epidermis.

For the production of the TTS of the invention, the skilled worker is thus able in principle to have recourse to the materials, production methods and structure of the TTS or transdermal patches which are known in the prior art and which additionally include according to the invention a suitable means/agent combination (cf., for example, transdermal plaster; Spektrum der Wissenschaft 10/2003, 42; Transdermal Controlled Systemic Madications, Y. W. Chien, Drugs and the Pharmaceutical Sciences, Vol. 31; Polymers in Transdermal Drug Delivery Systems, S. Kandavilli et al., Pharmaceutical Technology, May 2002, 62-80). The precondition for the suitability of a plastic for such medical applications is besides favorable material properties (e.g. mechanical strength and processability), for hygienic reasons in particular its good sterilizability. These requirements are satisfied for example by polyethylene, polypropylene, polyvinyl chloride, polystyrene, polymethacrylates, polyamides and polycarbonates.

The invention is explained in more detail by the following example without being restricted thereto. It is nevertheless possible for specific configurations of the TTS of the invention which are described in the example to be generalized as such individually or in combination with one another as preferred features of the invention.

EXAMPLE 1

100 g of levulinic acid, 150 g of oleyl oleate, 100 g of polyvinylpyrrolidone, 150 g of ethanol, 200 g of ethyl acetate and 100 g of buprenorphine base are added to 1.14 kg of a solution of a self-crosslinking polyacrylate consisting of the monomers 2-ethylhexyl acrylate, vinyl acetate, butyl acrylate and acrylic acid in the mixture of the organic solvents ethyl acetate, heptane and isopropanol/toluene, and this mixture is stirred for about 2 hours until homogeneous. After the homogenization, the mixture is spread on the siliconized side of a 100 µm polyester film, and the solvent is removed in a drying oven by drying at 60 or 80° C. for 10 minutes. The spreading thickness in the coating was chosen so that a weight per unit area of about 80 g/m$^2$ results after removal of the solvent. After removal of the solvent, the laminate consisting of siliconized polyester film and active ingredient-containing polymer layer is covered with an absorbent material, e.g. blotting paper or a nonwoven. The complete laminate is then cut into squares of edge length 5×5 cm. The siliconized polyester film 5×5 cm in size is removed and the laminate of buprenorphine-containing adhesive layer and nonwoven is placed on the siliconized side of a further polyester film in such a way that the polyester film projects all round beyond the active ingredient-containing adhesive layer covered with absorbent rigid nonwoven. A five-pointed star made of rigid plastic material is then placed on the nonwoven. A bag which is filled with potassium permanganate solution and which is designed to have a smaller total area than the active ingredient-containing polymer layer is placed on the absorbent nonwoven. Without limiting the invention, the bag may have dimensions of 4×4 cm. In a second step, a laminate consisting of siliconized paper, active ingredient-free pressure-sensitive adhesive layer and polyester film 23 µm has previously been produced. The siliconized paper is removed, and the intermediate product consisting of siliconized polyester film, the square consisting of active ingredient-containing polymer layer with absorbent nonwoven and star, covered by a polyethylene bag 4×4 cm in size and filled with potassium permanganate solution is covered, and then the TTS are cut out in such a manner that the active ingredient-free pressure-sensitive adhesive layer projects all round beyond the active ingredient-containing pressure-sensitive adhesive layer.

If the TTS is now applied it is initially necessary to remove the siliconized polyester layer (release liner), which is easily possible. If the TTS is stuck onto a patient's skin, the bag filled with aqueous potassium permanganate solution remains undamaged. If, however, after the application time of 2-7 days the TTS is removed from the patient's skin, at least one point of the five-pointed star pierces, owing to the rigidity, the bag with potassium permanganate solution and inevitably destroys it. The geometry of the star ensures that the bag tears in every case, irrespective of the direction in which the TTS is removed from the patient. The potassium permanganate solution disperses through the absorbent nonwoven over the area of the TTS within a short time. An oxidation process is started thereby and, in the case of, for example, buprenorphine leads to its destruction by oxidation. Even if the worn TTS is subjected to extraction immediately after removal of the TTS, this decomposition process can no longer be halted; on the contrary it is accelerated by first the opiate buprenorphine and the oxidizing agent potassium permanganate being brought into solution. It is thus ensured that the active ingredient cannot be abused.

The transdermal patch described in the example thus has the following (layer) structure (1-6):
6 polyester film with active ingredient-free pressure-sensitive adhesive layer
5 plastic star
4 potassium permanganate solution (bag)
3 nonwoven
2 active ingredient-containing pressure-sensitive adhesive layer
1 siliconized polyester layer (release liner)
0 skin

The invention claimed is:
1. A transdermal therapeutic system (TTS) comprising an active ingredient, an agent which can render the active ingredient inactive, and a star-shaped piercing means by which the active ingredient and the agent are brought into contact with one another when removing the TTS from a patient's skin thereby destroying the active ingredient.
2. The transdermal therapeutic system as claimed in claim 1, wherein the TTS is a transdermal patch.

3. The transdermal therapeutic system as claimed in claim 1, wherein the active ingredient and agent are spatially separate from one another.

4. The transdermal therapeutic system as claimed in claim 1, wherein the active ingredient and agent react chemically together after removal of the TTS from the patient's skin.

5. The transdermal therapeutic system as claimed in claim 1, wherein the active ingredient is an analgesic.

6. The transdermal therapeutic system as claimed in claim 1, wherein the active ingredient is a narcotic.

7. The transdermal therapeutic system as claimed in claim 1, wherein the active ingredient is a morphine derivative, heroin or buprenorphine.

8. The transdermal therapeutic system as claimed in claim 1, wherein the active ingredient is fentanyl, sufentanyl or alfentanyl.

9. The transdermal therapeutic system as claimed in claim 1, wherein the agent is an oxidizing agent.

10. The transdermal therapeutic system as claimed in claim 1, wherein the agent is potassium permanganate.

11. The transdermal therapeutic system as claimed in claim 1, wherein the active ingredient is buprenorphine and the agent is potassium permanganate.

12. A pain therapy method comprising applying a transdermal therapeutic system as claimed in claim 1.

13. The transdermal therapeutic system as claimed in claim 1, wherein said agent is a solution disposed in a hag and said means pierces said bag when the transdermal therapeutic system is removed.

14. A transdermal therapeutic system comprising an active ingredient, an agent which can render the active ingredient inactive, and a star-shaped piercing means by which the active ingredient and the agent are brought into contact with one another by removing the TTS from a patient's skin thereby destroying the active ingredient, wherein
    said active ingredient is contained within a polymer layer disposed upon a siliconized film;
    an absorbent material is disposed upon the active-ingredient-containing-polymer-layer on a side opposing the siliconized film;
    a rigid star-shaped piercing means by which the active ingredient and the agent are brought into contact with one another during removal of the TTS is disposed upon the absorbent material,
    a bag filled with a solution containing the agent which can render the active ingredient inactive is disposed upon the means by which the active ingredient and the agent are brought into contact with one another and pierced thereby during removal of the TTS;
    an active-ingredient-free adhesive layer is disposed on the bag that projects all round beyond the active-ingredient-containing-polymer layer and
    a film is disposed on the active-ingredient-free adhesive layer.

* * * * *